(12) United States Patent
Johannessen et al.

(10) Patent No.: US 7,786,070 B2
(45) Date of Patent: *Aug. 31, 2010

(54) SUBCUTANEOUS ADMINISTRATION OF COAGULATION FACTOR VII

(75) Inventors: Marie Johannessen, Birkerod (DK); Ole Juul Nordfang, Hillerod (DK); Jens Aas Jansen, Charlottenlund (DK)

(73) Assignee: Novo Nordisk HealthCare A/G, Zurich (CH)

( * ) Notice: Subject to any disclaimer, the term of this patent is extended or adjusted under 35 U.S.C. 154(b) by 1454 days.

This patent is subject to a terminal disclaimer.

(21) Appl. No.: 10/283,751

(22) Filed: Oct. 30, 2002

(65) Prior Publication Data

US 2008/0145914 A1    Jun. 19, 2008

Related U.S. Application Data

(63) Continuation of application No. PCT/DK01/00302, filed on May 2, 2001, and a continuation-in-part of application No. 10/026,032, filed on Oct. 25, 2001, now Pat. No. 6,833,352.

(30) Foreign Application Priority Data

Mar. 22, 2001  (DK) ............................... 2001 00477

(51) Int. Cl.
  *C12N 9/50*  (2006.01)
(52) U.S. Cl. ............................................ 514/2; 435/219
(58) Field of Classification Search .................. None
  See application file for complete search history.

(56) References Cited

U.S. PATENT DOCUMENTS

| 4,456,591 A | 6/1984 | Thomas ...................... 424/101 |
| 4,479,938 A | 10/1984 | Thomas ...................... 424/101 |
| 5,180,583 A | 1/1993 | Hedner ........................ 424/94 |
| 5,374,617 A | 12/1994 | Morrissey et al. .............. 514/8 |
| 5,925,739 A | 7/1999 | Spira et al. .................. 530/383 |
| 6,310,183 B1 * | 10/2001 | Johannessen et al. ....... 530/384 |
| 6,833,352 B2 * | 12/2004 | Johannessen et al. .......... 514/2 |
| 2002/0137673 A1 | 9/2002 | Pingel et al. |
| 2003/0054018 A1 | 3/2003 | Hedner |
| 2003/0104978 A1 | 6/2003 | Persson et al. |
| 2003/0199444 A1 | 10/2003 | Knudsen et al. |

FOREIGN PATENT DOCUMENTS

| WO | WO 93/07890 | 4/1993 |
| WO | WO 95/26750 | 10/1995 |
| WO | WO 95/28954 | 11/1995 |
| WO | WO 96/12800 | 5/1996 |
| WO | WO 2004/000366 | 12/2003 |

OTHER PUBLICATIONS

Brinkhouse et al., Proc. Natl. Acad. Sci. USA, 1989, vol. 86, pp. 1382-1386.*
Dunn et al., Biodrugs. vol. 12. No. 1. pp. 71-77 (1999).

* cited by examiner

*Primary Examiner*—Christopher R. Tate
*Assistant Examiner*—Roy Teller
(74) *Attorney, Agent, or Firm*—Reza Green

(57) ABSTRACT

The invention relates to the use of a Factor VIIa for the manufacture of a medicament for treatment of a condition affectable by Factor VIIa, said medicament being for subcutaneous, intramuscular or intradermal administration, and to the use of a Factor VIIa for the manufacture of a medicament for treatment of a condition affectable by Factor VIIa, wherein said medicament, when administered subcutaneously, intradermally or intramuscularly, shows a prolonged biological half-life.

8 Claims, 6 Drawing Sheets

Figure 1A:
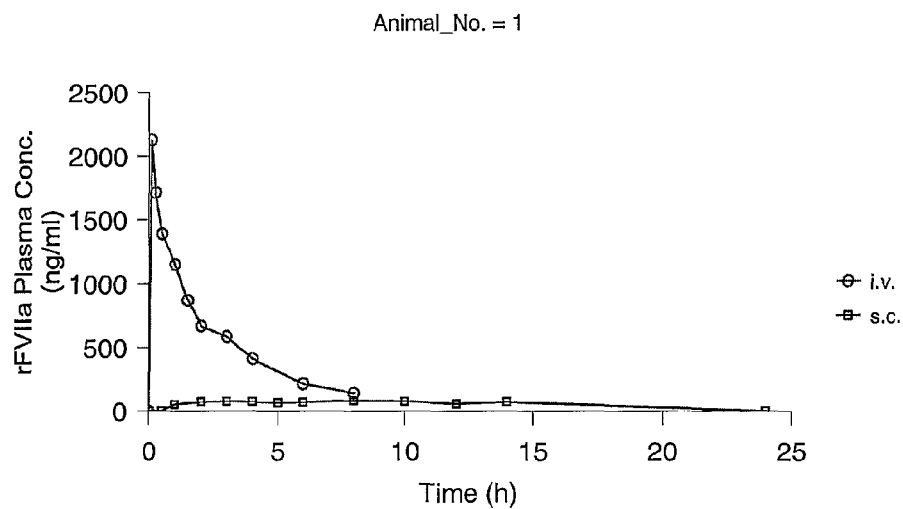
Figure 1B:
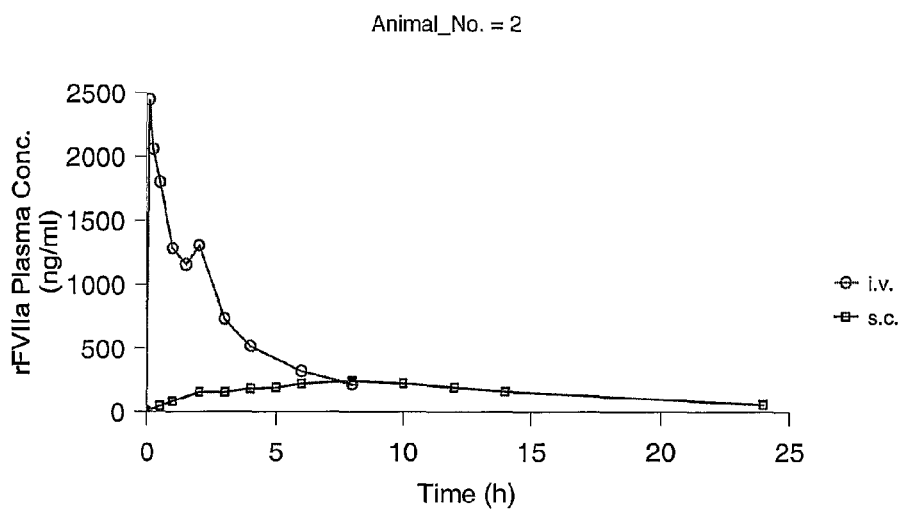
Figure 1C:
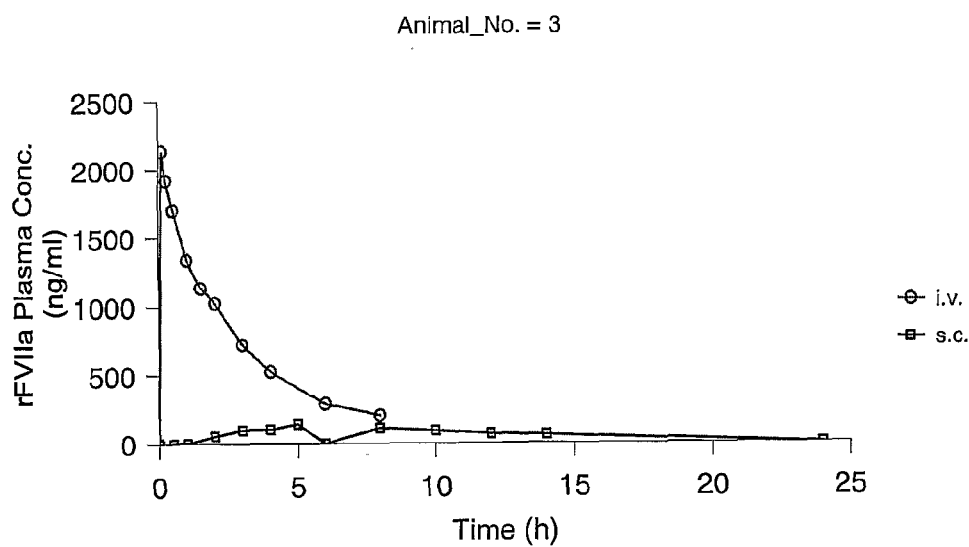
Figure 1D:
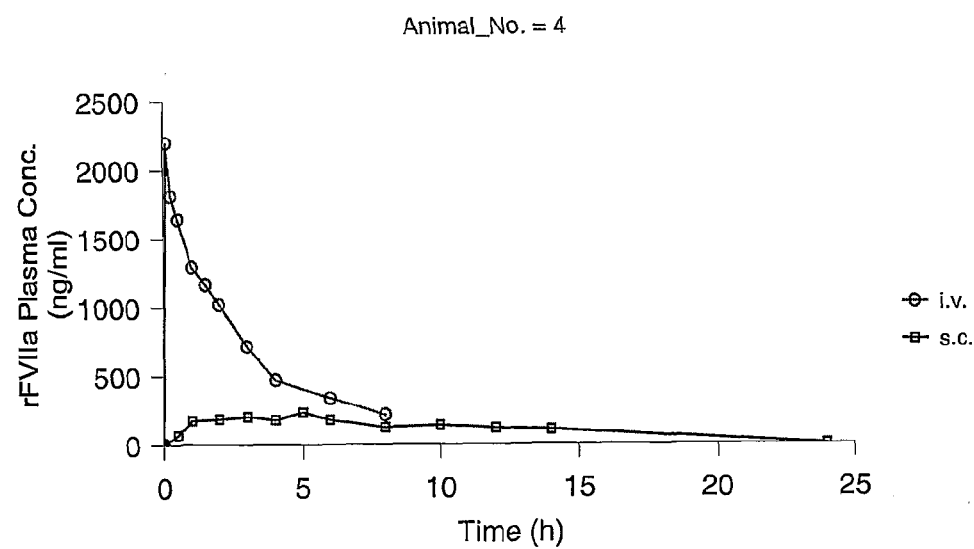
Figure 2A:
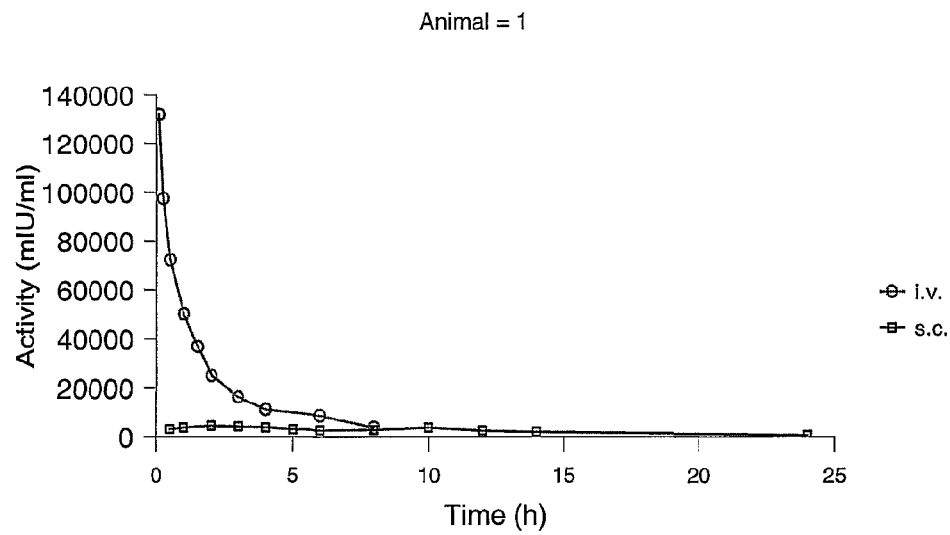
Figure 2B:
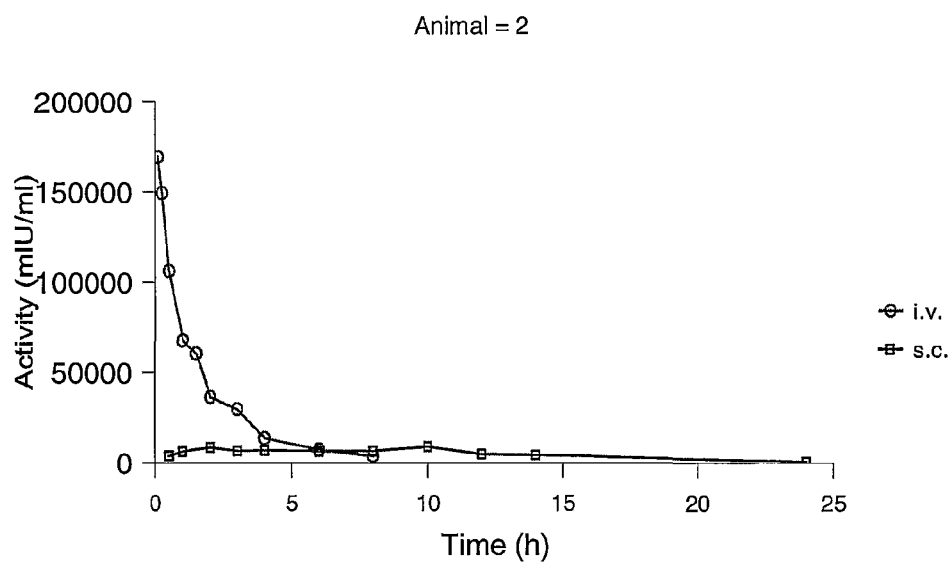
Figure 2C:
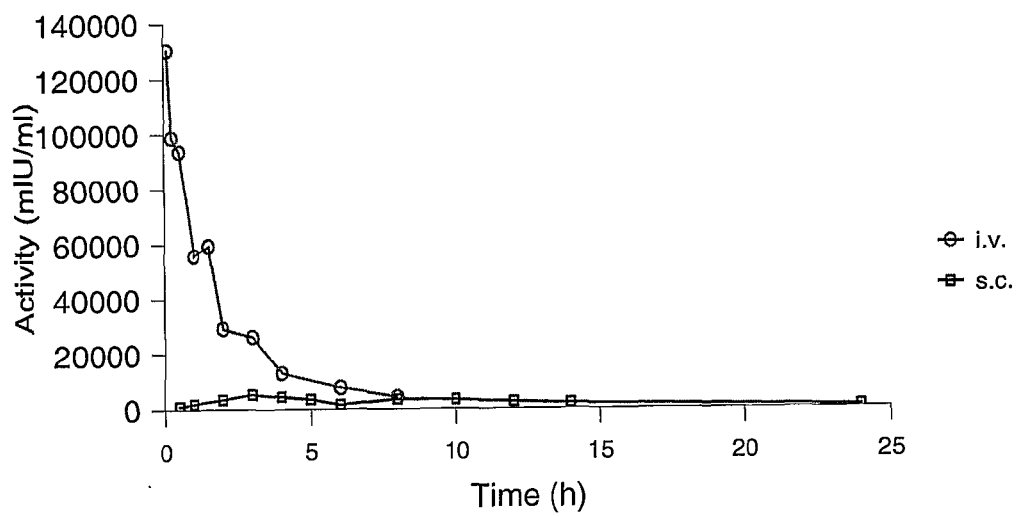
Figure 2D:
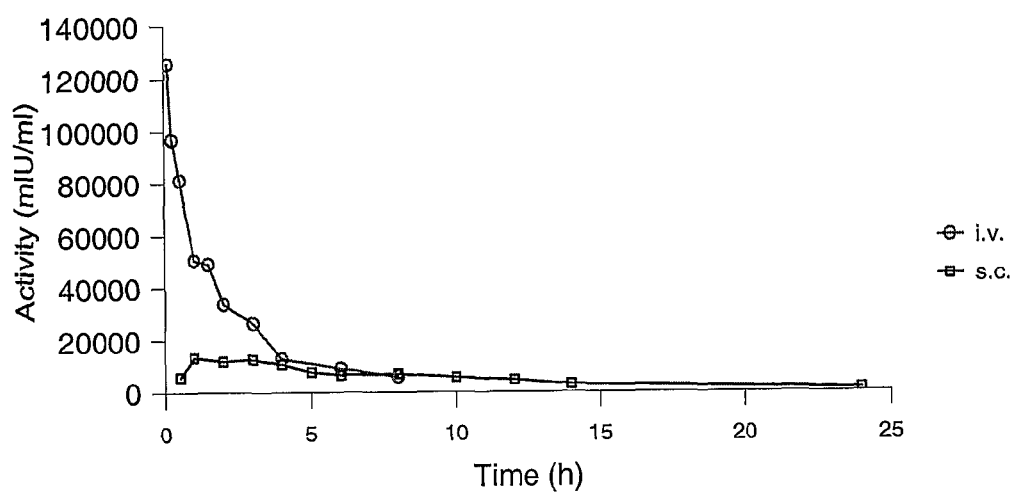

Figure 1. Individual Plasma Concentration Profiles of rFVIIa Following Intravenous (i.v.) and Subcutanous (s.c.) Administration of 0.2 mg/kg to Minipigs Figure 2. Individual Plasma Activity Profiles of rFVIIa Following Intravenous (i.v.) and Subcutanous (s.c.) Administration of 0.2 mg/kg to Minipigs The amino acid sequence of native human coagulation Factor VII (wild-type Factor VII):

Ala-Asn-Ala-Phe-Leu-GLA-GLA-Leu-Arg-Pro-Gly-Ser-Leu-GLA-Arg-GLA-Cys-Lys-
　　　　　　5　　　　　　　　10　　　　　　　　15

GLA-GLA-Gln-Cys-Ser-Phe-GLA-GLA-Ala-Arg-GLA-Ile-Phe-Lys-Asp-Ala-GLA-Arg-
　　20　　　　　　　25　　　　　　　30　　　　　　　35

Thr-Lys-Leu-Phe-Trp-Ile-Ser-Tyr-Ser-Asp-Gly-Asp-Gln-Cys-Ala-Ser-Ser-Pro-
　　　　　　40　　　　　　　　45　　　　　　　50

Cys-Gln-Asn-Gly-Gly-Ser-Cys-Lys-Asp-Gln-Leu-Gln-Ser-Tyr-Ile-Cys-Phe-Cys-
55　　　　　　　60　　　　　　　65　　　　　　　70

Leu-Pro-Ala-Phe-Glu-Gly-Arg-Asn-Cys-Glu-Thr-His-Lys-Asp-Asp-Gln-Leu-Ile-
　　　75　　　　　　　　80　　　　　　　　85　　　　　　　　90

Cys-Val-Asn-Glu-Asn-Gly-Gly-Cys-Glu-Gln-Tyr-Cys-Ser-Asp-His-Thr-Gly-Thr-
　　　　　　95　　　　　　　　100　　　　　　　105

Lys-Arg-Ser-Cys-Arg-Cys-His-Glu-Gly-Tyr-Ser-Leu-Leu-Ala-Asp-Gly-Val-Ser-
　　110　　　　　　　115　　　　　　　120　　　　　　　125

Cys-Thr-Pro-Thr-Val-Glu-Tyr-Pro-Cys-Gly-Lys-Ile-Pro-Ile-Leu-Glu-Lys-Arg-
　　　　　　130　　　　　　　　135　　　　　　　140

Asn-Ala-Ser-Lys-Pro-Gln-Gly-Arg-Ile-Val-Gly-Gly-Lys-Val-Cys-Pro-Lys-Gly-
145　　　　　　　150　　　　　　　155　　　　　　　160

Glu-Cys-Pro-Trp-Gln-Val-Leu-Leu-Leu-Val-Asn-Gly-Ala-Gln-Leu-Cys-Gly-Gly-
　　　　　　165　　　　　　　　170　　　　　　　175　　　　　　　180

Thr-Leu-Ile-Asn-Thr-Ile-Trp-Val-Val-Ser-Ala-Ala-His-Cys-Phe-Asp-Lys-Ile-
　　　　　　185　　　　　　　　190　　　　　　　195

Lys-Asn-Trp-Arg-Asn-Leu-Ile-Ala-Val-Leu-Gly-Glu-His-Asp-Leu-Ser-Glu-His-
　　200　　　　　　　205　　　　　　　210　　　　　　　215

FIG. 3

Asp-Gly-Asp-Glu-Gln-Ser-Arg-Arg-Val-Ala-Gln-Val-Ile-Ile-Pro-Ser-Thr-Tyr-
    220               225              230

Val-Pro-Gly-Thr-Thr-Asn-His-Asp-Ile-Ala-Leu-Leu-Arg-Leu-His-Gln-Pro-Val-
235          240           245           250

Val-Leu-Thr-Asp-His-Val-Val-Pro-Leu-Cys-Leu-Pro-Glu-Arg-Thr-Phe-Ser-Glu-
    255           260           265           270

Arg-Thr-Leu-Ala-Phe-Val-Arg-Phe-Ser-Leu-Val-Ser-Gly-Trp-Gly-Gln-Leu-Leu-
       275          280         285

Asp-Arg-Gly-Ala-Thr-Ala-Leu-Glu-Leu-Met-Val-Leu-Asn-Val-Pro-Arg-Leu-Met-
  290         295         300         305

Thr-Gln-Asp-Cys-Leu-Gln-Gln-Ser-Arg-Lys-Val-Gly-Asp-Ser-Pro-Asn-Ile-Thr-
    310          315         320

Glu-Tyr-Met-Phe-Cys-Ala-Gly-Tyr-Ser-Asp-Gly-Ser-Lys-Asp-Ser-Cys-Lys-Gly-
325         330         335         340

Asp-Ser-Gly-Gly-Pro-His-Ala-Thr-His-Tyr-Arg-Gly-Thr-Trp-Tyr-Leu-Thr-Gly-
  345         350         355         360

Ile-Val-Ser-Trp-Gly-Gln-Gly-Cys-Ala-Thr-Val-Gly-His-Phe-Gly-Val-Tyr-Thr-
     365         370         375

Arg-Val-Ser-Gln-Tyr-Ile-Glu-Trp-Leu-Gln-Lys-Leu-Met-Arg-Ser-Glu-Pro-Arg-
380         385         390         395

Pro-Gly-Val-Leu-Leu-Arg-Ala-Pro-Phe-Pro
    400         405 406

FIG. 3 CONTINUED

SUBCUTANEOUS ADMINISTRATION OF COAGULATION FACTOR VII

CROSS-REFERENCE TO RELATED APPLICATIONS

This application is a continuation of application serial no. PCT/DK01/00302 filed on May 2, 2001 and a continuation-in-part of U.S. application Ser. No. 10/026,032 filed on Oct. 25, 2001 now U.S. Pat. No. 6,833,352 and claims priority under 35 U.S.C. 119 of U.S. application Ser. No. 09/148,440 filed on Sep. 4, 1998; Danish application no. 1038/97 filed on Sep. 10, 1997; U.S. provisional application Ser. No. 60/059,236 filed on Sep. 18, 1997; Danish application no. PA 2000 00734 filed on May 3, 2000; Danish application no. PA 2000 01360 filed on Sep. 13, 2000; Danish application no. PA 2000 01361 filed on Sep. 13, 2000, and Danish application no. PA 2001 00477, filed on Mar. 22, 2001, the contents of which are fully incorporated herein by reference.

FIELD OF INVENTION

The invention relates to the use of coagulation Factor VIIa for the manufacture of a medicament for prevention or treatment of conditions affectable by Factor VIIa, wherein the medicament is for subcutaneous, intramuscular or intradermal administration. The invention further relates to the use of coagulation Factor VIIa for the manufacture of a medicament for treatment of a condition affectable by Factor VIIa, wherein said medicament, when administered subcutaneously, intradermally or intramuscularly, shows a prolonged biological half-life.

BACKGROUND OF INVENTION

Blood coagulation is a process consisting of a complex interaction of various blood components, or Factors, which eventually gives rise to a fibrin clot. Generally, the blood components which participate in what has been referred to as the coagulation "cascade" are proenzymes or zymogens, enzymatically inactive proteins which are converted to proteolytic enzymes by the action of an activator, itself an activated clotting Factor. Coagulation Factors that have undergone such a conversion are generally referred to as "active Factors", and are designated by the addition of a lower case "a" suffix (e.g., Factor VIIa).

Activated Factor X ("Xa") is required to convert prothrombin to thrombin, which then converts fibrinogen to fibrin as a final stage in forming a fibrin clot. There are two systems, or pathways, that promote the activation of Factor X. The "intrinsic pathway" refers to those reactions that lead to thrombin formation through utilisation of Factors present only in plasma. A series of protease-mediated activations ultimately generates Factor IXa that, in conjunction with Factor VIIIa, cleaves Factor X into Xa. An identical proteolysis is affected by Factor VIIa and its co-Factor, tissue Factor, in the "extrinsic pathway" of blood coagulation. Tissue Factor is a membrane bound protein and does not normally circulate in plasma. Upon vessel disruption, however, it can complex with Factor VIIa to catalyse Factor X activation or Factor IX activation in the presence of $Ca^{++}$ and phospholipid. While the relative importance of the two coagulation pathways in haemostasis is unclear, in recent years Factor VII and tissue Factor have been found to play a pivotal role in the regulation of blood coagulation.

Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa or thrombin in vitro. Factor Xa is believed to be the major physiological activator of Factor VII. Like several other plasma proteins involved in haemostasis, Factor VII is dependent on vitamin K for its activity, which is required for the γ-carboxylation of multiple glutamic acid residues that are clustered in the amino terminus of the protein. These γ-carboxylated glutamic acids are required for the metal-associated interaction of Factor VII with phospholipids.

The conversion of zymogen Factor VII into the activated two-chain molecule occurs by cleavage of an internal peptide bond located approximately in the middle of the molecule. In human Factor VII, the activation cleavage site is at $Arg_{152}$-$Ile_{153}$. In the presence of tissue Factor, phospholipids and calcium ions, the two-chain Factor VIIa rapidly activates Factor X or Factor IX by limited proteolysis.

Coagulation Factors are large proteins that are normally given intravenously to make the medicament directly available in the bloodstream. It would however be advantageous if a medicament could be given subcutaneously, intramuscularly or intradermally as these administration forms are much easier to handle for the patient, especially if the medicament must be taken regularly during the whole life and treatment is to start early, e.g. when the patient is a child. However, a medicament with a very large and labile molecule normally has a low bioavailability if given subcutaneously, intramuscularly or intradermally, since the uptake is low and degradation is severe. Furthermore, such large proteins may be immunogenic when administered subcutaneously.

Recombinant human Factor VIIa (rFVIIa) is an activated coagulation Factor that is useful in the treatment of haemophiliacs that generate neutralising antibodies against Factor VIII or Factor IX. Factor VIII and Factor IX causes severe antibody formation in approximately 10% of the haemophilia patients. The action of rFVIIa (activation of the coagulation system via Factor X) is exerted in the vascular compartment of the body. The route of administration of rFVIIa has until now been intravenously. As a result of the relatively short half-life, administration normally has to be repeated every 2.5 to 3 hours. An alternative form of administration which would result in a reasonable bioavailability and a long lasting absorption phase would allow an increase in dosing intervals and at the same time make self administration possible, thus increasing the convenience for the patient.

Factor VIIa is a glycoprotein with a molecular weight of approximately 50 kDa. It is therefore a sufficiently large molecule to point to the need for direct introduction into the bloodstream, since a very low bioavailability, if any, would be expected. Furthermore quite large doses may be required for an adult, for example during surgery. Consequently, Factor VIIa has conventionally been delivered intravenously to haemophilia A or B patients, either prophylactically or in response to bleeding episodes. Such repeated use of intravenous injections, while necessary to control the disease, may have side effects. Repeated injections may lead to the vein at the site of injection becoming fibrosed or occluded, a problem especially acute when treating the elderly. Also, when veins are small, as in babies, it may be difficult for the doctor to insert a needle into the vein to inject the required therapeutic dose.

The only coagulation Factor proteins that have been administered by subcutaneous injection are Factors VIII (170-300 kDa) and IX (60 kDa). These coagulation Factors are administered in the form of the single-chain zymogens, which have not yet been activated. These non-activated forms are more stable than the activated (cleaved) forms, which are degraded much faster. Subcutaneous injection of these two proteins does not significantly change their pharmacokinetic properties (e.g., half life).

It has now been found that the activated, cleaved and thus more labile form of coagulation Factor VIIa can be delivered by subcutaneous, intramuscular or intradermal injection with sufficiently transport into the bloodstream in biologically active form and in adequate concentrations. It has also been found that FVIIa shows favourable pharmacokinetic properties (especially half life) when injected subcutaneously, intramuscularly or intradermally.

Factor VIIa is useful for administration to mammals, particularly humans, to control bleeding disorders, particularly bleeding disorders which are caused by clotting Factor deficiencies (haemophilia A and B), or clotting Factor inhibitors or bleeding disorders in patients not suffering from haemophilia A or B, for example, in patients suffering from von Willebrand's disease. Patients with von Willebrand's disease have a defective primary haemostasis because they lack or have an abnormal von Willebrand Factor protein. Bleeding disorders are also seen in patients with a normally functioning blood clotting cascade and may be caused by a defective platelet function, thrombocytopenia, or even by unknown reasons. Furthermore, FVIIa may be used for preventing or treating excessive bleedings in patients where the haemostatic system including the coagulation cascade and platelets is functioning normally. Such excessive bleedings are, for example, bleedings in association with tissue damage, for example surgery or trauma, especially in tissues rich in tissue Factor (TF). FVIIa may be used in such situations as well as when the bleeding is diffuse and poorly responding to current haemostatic techniques and therapies (e.g. haemorrhagic gastritis and profuse uterine bleeding). FVIIa may also be suitable for the treatment of bleedings occurring in organs with limited possibility for mechanical haemostasis such as brain, inner ear region, eyes as well as in association with the process of taking biopsies from various organs and in laparoscopic surgery.

BACKGROUND ART

International Patent Application No. WO 93/07890 relates to the treatment of haemophilia with FIX by subcutaneous injection.

International Patent Application No. WO 95/26750 relates to a formulation of FVIII or FIX suitable for subcutaneous injection for treatment of haemophilia A or B.

International Patent Application No. WO 95/28954 relates to concentrated preparations of FIX suitable for storage and subcutaneous injection.

LIST OF FIGURES

FIG. 1a-d shows the Individual Plasma Concentration Profiles of rFVIIa Following Intravenous (i.v.) and Subcutanous (s.c.) Administration of 0.2 mg/kg to Minipigs Nos. a-d;

FIG. 2a-d shows the Individual Plasma Activity Profiles of rFVIIa Following Intravenous (i.v.) and Subcutanous (s.c.) Administration of 0.2 mg/kg to Minipigs Nos. a-d;

FIG. 3 shows the amino acid residue sequence of wild-type Factor VII.

LIST OF TABLES

Table 1 shows the PK-Results from ELISA-Assay following Dosing 0.2 mg/kg (0.33 ml/kg) rFVII i.v. and s.c. to Minipigs Weighing 11.4-13.4 kg.

Table 2 shows the PK-Results from Clot-Assay Following Dosing 0.2 mg/kg (0.33 ml/kg) rFVII i.v. and s.c. to Minipigs Weighing 11.4-13.4 kg.

SUMMARY OF THE INVENTION

It has now been found that activated coagulation Factor VIIa, (Factor VIIa or FVIIa), which is a very sensitive protein, can be administered subcutaneously, intramuscularly or intradermally, showing an acceptable absorption and a high level of active Factor VIIa protein in the blood. Furthermore, the plasma half life of both FVII antigen and FVII activity is increased significantly by the above administration and the t(max) is delayed by several hours.

Thus, in one aspect, the invention provides the use of a Factor VIIa for the manufacture of a medicament for treatment of a condition affectable by FVIIa, said medicament being for subcutaneous, intramuscular or intradermal administration In another aspect, the invention provides the use of a Factor VIIa for the manufacture of a medicament for treatment of a condition affectable by FVIIa, wherein said medicament, when administered subcutaneously, intradermally or intramuscularly, shows a prolonged biological half-life.

In one embodiment, the invention provides the use of a Factor VIIa as the sole active coagulation factor for the manufacture of a medicament for treatment of a condition affectable by FVIIa, said medicament being for subcutaneous, intramuscular or intradermal administration In another embodiment, the invention provides the use of a Factor VIIa as the sole active coagulation factor for the manufacture of a medicament for treatment of a condition affectable by FVIIa, wherein said medicament, when administered subcutaneously, intradermally or intramuscularly, shows a prolonged biological half-life.

In one embodiment of the invention, the Factor VIIa is recombinant human Factor VIIa. In another embodiment, the Factor VIIa is an amino acid sequence variant of Factor VIIa.

In one embodiment, the Factor VIIa variants having substantially the same or improved biological activity relative to wild-type Factor VIIa are those that exhibit at least about 25%, preferably at least about 50%, more preferably at least about 75% and most preferably at least about 90% of the specific activity of Factor VIIa that has been produced in the same cell type, when tested in one or more of a clotting assay, proteolysis assay, or TF binding assay as described in the present specification. In one embodiment, the Factor Vila variants are selected from the list of [L305V]-FVIIa, [L305V/M306D/D309S]-FVIIa, [L305I]-FVIIa, [L305T]-FVIIa, [F374P]-FVIIa, [V158T/M298Q]-FVIIa, [V158D/E296V/M298Q]-FVIIa and [K337A]-FVIIa.

In one embodiment, the medicament is for subcutaneous administration. In another embodiment, the medicament is for intramuscular administration. In another embodiment, the medicament is for intradermal administration.

In one embodiment, the medicament is in the form of a ready-to use aqueous solution. In another embodiment, the medicament is in the form of a lyophilised composition that prior to administration has been reconstituted in a pharmaceutically acceptable vehicle suitable for injection.

In one embodiment of the invention, the condition affectable by Factor VIIa is bleeding caused by lack of or defective coagulation Factors VII, IX or VII, or by inhibitors against coagulation Factors VIII, IX or VII. In another embodiment, the condition is bleeding caused by a defective platelet function. In yet another embodiment, the condition is bleeding associated with excessive tissue damage or trauma.

The subject suffering from a condition affectable by Factor VIIa may be any animal, in particular a mammal—in a preferred embodiment, the mammal is a human being.

DETAILED DESCRIPTION OF THE INVENTION

Definitions

Factor VIIa, or FVIIa, may be purified from blood or produced by recombinant means. It is evident that the practice of the methods described herein is independent of how the purified Factor VIIa is derived and, therefore, the present invention is contemplated to cover use of any Factor VIIa preparation suitable for use herein.

As used herein, "Factor VIIa" encompasses wild-type Factor VII (i.e., a polypeptide having the amino acid sequence disclosed in U.S. Pat. No. 4,784,950), as well as variants of Factor VII exhibiting substantially the same or improved biological activity relative to wild-type Factor VII. The term "Factor VIIa" is intended to encompass Factor VII polypeptides that have been proteolytically processed to yield their respective bioactive forms. Typically, Factor VII is cleaved between residues 152 and 153 to yield Factor VIIa.

The biological activity of Factor VIIa in blood clotting derives from its ability to (i) bind to tissue Factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce of Factor Xa in a system comprising TF embedded in a lipid membrane and Factor X. (Persson et al., *J. Biol. Chem.* 272:19919-19924, 1997); (ii) measuring Factor X hydrolysis in an aqueous system; (iii) measuring its physical binding to TF using an instrument based on surface plasmon resonance (Persson, *FEBS Letts.* 413:359-363, 1997) and (iv) measuring hydrolysis of a synthetic substrate.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of Factor VIIa that has been produced in the same cell type, when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity.

Variants of Factor VII, whether exhibiting substantially the same or better bioactivity than wild-type Factor VII, include, without limitation, polypeptides having an amino acid sequence that differs from the sequence of wild-type Factor VII by insertion, deletion, or substitution of one or more amino acids. Non-limiting examples of Factor VII variants having substantially the same biological activity as wild-type Factor VII include [S52A]-FVIIa, [S60A]-FVIIa (Iino et al., *Arch. Biochem. Biophys.* 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., *Biotechnol. Bioeng.* 48:501-505, 1995); and oxidized forms of Factor VIIa (Kornfelt et al., *Arch. Biochem. Biophys.* 363:43-54, 1999). Non-limiting examples of Factor VII variants having substantially the same or better biological activity compared to wild-type Factor VIIa include, but are not limited to, those described in Danish Patent Applications Nos. PA 2000 00734, PA 2000 01360, PA 2000 01361, and PA 2001 00477. Non-limiting examples include [L305V]-FVIIa, [L305V/M306D/D309S]-FVIIa, [L305I]-FVIIa, [L305T]-FVIIa, [F374P]-FVIIa, [V158T/M298Q]-FVIIa, [V158D/E296V/M298Q]-FVIIa and [K337A]-FVIIa.

In the present context the three-letter or one-letter indications of the amino acids have been used in their conventional meaning as indicated in table 1. Unless indicated explicitly, the amino acids mentioned herein are L-amino acids. It is to be understood, that the first letter in, for example, K337 represent the amino acid naturally present at the indicated position of FIG. 3, and that, for example, [K337A]-FVIIa designates the FVII-variant wherein the amino acid represented by the one-letter code K naturally present in the indicated position in FIG. 3 is replaced by the amino acid represented by the one-letter code A.

TABLE 1

| Abbreviations for amino acids: | | |
|---|---|---|
| Amino acid | Tree-letter code | One-letter code |
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |

In this context, the term "a FVIIa unit" is defined by calibration against a secondary standard of the First International Standard 89/688 established in 1993. 50 international units (IU) human wild-type FVIIa correspond to about 1 µg protein.

In this context, the term "treatment" is designated to include prophylactic treatment of a FVIIa affectable condition.

| Abbreviations | |
|---|---|
| TF | tissue Factor |
| FVII | Factor VII in its single-chain, unactivated form |
| FVIIa | Factor VII in its activated form |
| rFVIIa | recombinant Factor VII in its activated form |
| FVIII | Factor VIII in its unactivated form |
| FIX | Factor IX in its unactivated form |
| IU | International Units |

Preparation of Compound

Human purified Factor VIIa suitable for use in the present invention is preferably made by DNA recombinant technology, e.g. as described by Hagen et al., *Proc. Natl. Acad. Sci. USA* 83: 2412-2416, 1986 or as described in European Patent No. 200.421 (ZymoGenetics).

The Factor VII variants described herein may be produced by means of recombinant nucleic acid techniques. In general, a cloned wild-type Factor VII nucleic acid sequence is modified to encode the desired protein. This modified sequence is then inserted into an expression vector, which is in turn transformed or transfected into host cells. Higher eukaryotic cells, in particular cultured mammalian cells, are preferred as host cells. The complete nucleotide and amino acid sequences for human Factor VII are known (see U.S. Pat. No. 4,784,950, where the cloning and expression of recombinant human Factor VII is described). The bovine Factor VII sequence is described in Takeya et al., *J. Biol. Chem.* 263:14868-14872 (1988)).

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of Factor VII, one may introduce the alteration(s) of choice. Likewise, procedures for preparing a DNA construct using polymerase chain reaction using specific primers are well known to persons skilled in the art (cf. PCR Protocols, 1990, Academic Press, San Diego, Calif., USA).

Factor VII may also be produced by the methods described by Broze and Majerus, *J. Biol. Chem.* 255 (4): 1242-1247, 1980 and Hedner and Kisiel, *J. Clin. Invest.* 71: 1836-1841, 1983. These methods yield Factor VII without detectable amounts of other blood coagulation Factors. An even further purified Factor VII preparation may be obtained by including an additional gel filtration as the final purification step. Factor VII is then converted into activated FVIIa by known means, e.g. by several different plasma proteins, such as Factor XIIa, IX a or Xa. Alternatively, as described by Bjoern et al. (Research Disclosure, 269 September 1986, pp. 564-565), Factor VII may be activated by passing it through an ion-exchange chromatography column, such as Mono Q® (Pharmacia fine Chemicals) or the like.

Pharmaceutical Administration

The regimen for any patient to be treated with FVIIa as mentioned herein should be determined by those skilled in the art. The dose to be administered in therapy can be determined by a physician and will depend on the route of administration (subcutaneous, intramuscular or intradermal) and on the weight and the condition of the patient.

Where FVIIa injected intravenously normally has to be administered every 2.5-3 hours, FVIIa injected subcutaneously, intradermally or intramuscularly should be administered with an interval of 12-48 hours, preferably 24 hours. FVIIa is preferably administered by subcutaneous injections and in an amount of about 100-100,000 units per kg body weight, and preferably in an amount of about 250-25,000 units per kg body weight corresponding to about 5-500 µg/kg.

Formulation of Medicament

An intravenous injection is normally 5-20 ml. It is normally preferred that an injection given subcutanously is between 0.05 to 1 ml. The concentration of FVIIa must therefore be high in such a medicament.

The volume given can be more than 0.01 ml, suitable 0.1-2 ml, preferably 0.25-1.5 ml and more preferable 0.5-1 ml.

Additives increasing the bioavailability of FVIIa are suitably organic compounds per se, salts thereof, emulsions or dispersions containing organic compounds per se or salts thereof, e.g. dispersions of polar lipids, or any combination or sequence of addition thereof. Organic compounds useful in the invention are e.g. amino acids, peptides, proteins, and polysaccharides. Peptides include dipeptides, tripeptides, oligopeptides, such as collagen and gelatine. The collagen and gelatine is preferably hydrolysed. Polysaccharides include e.g. chitosans, cyclodextrins, starch, hyaluronic acids, dextrans, cellulose, and any derivatives, combinations and/or sequence of addition thereof. The starch is preferably hydrolysed. The emulsions include oil-in-water emulsions with oil as the dispersed phase and water-in-oil dispersions with oil as the continuous phase. The oil can be of vegetable or of animal origin or synthetically produced. Suitably, the vegetable oil of the emulsions is soybean oil or safflower oil, or any combination thereof. Suitably the polar liquids are one or more phospho- lipids or glycolipids or any combination thereof. The additives increasing the bioavailability of FVIIa could be added to the formulation before drying or upon reconstitution, or it could be added to a stable solution or dispersion containing FVIIa.

Before administration, one or more aqueous solutions or dispersions could be added, in any mixture or sequence, to the medicament of the present invention, which is a stable aqueous solution, a dispersion or in dried form.

The medicament could be in a dried form, preferably freeze-dried. Before administration, the dried product or composition can be reconstituted with an aqueous solution or a dispersion e.g. a suspension, a liposomal formulation or an emulsion.

The medicament can also be a stable aqueous solution ready for administration. It can also be a dispersion, e.g. a suspension, a liposomal formulation or an emulsion. The medicament is preferably given subcutanously. The FVIIa activity in the formulation is preferably from about 0.1 mg/ml to about 50 mg/ml, more preferred from about 0.3 mg/ml to about 25 mg/ml, more preferred from about 0.6 mg/ml to about 25 mg/ml, more preferred from about 0.6 mg/ml to about 15 mg/ml, more preferred from about 1 mg/ml to about 15 mg/ml, and even more preferred from about 3 mg/ml to about 15 mg/ml.

The medicament may also comprise salt in order to give an isotonic solution, e.g. NaCl, KCl, and/or it may comprise one or more other isotonicity establishing compounds, preferably in an amount of more than 1.0 mg/ml.

Calcium, or other divalent metal ions, e.g. zinc, is necessary for the maintenance of the FVIIa activity. It may be added as, for example, calcium chloride, but other salts such as calcium gluconate, calcium glubionate or calcium gluceptate may also be used. The medicament preferable comprises calcium chloride in an amount of more than 0.15 mg/ml.

An amino acid is preferably used to buffer the system and it also protects the protein if the formulation is freeze-dried. A suitable buffer could be glycine, lysine, arginine, histidine or glycylglycine, preferred is glycylglycine.

A non-ionic surfactant may also be present in the medicament. The surfactant is preferable chosen from block-copolymers, such as a poloxamer, e.g. poloxamer 188, or a polyoxyethylene sorbitan fatty acid ester, such as polyoxyethylene-(20)-sorbitan monolaurate or polyoxyethylene-(20)-sorbitan monooleate. Preferred are polyoxyethylene-(20)-sorbitan monooleate (Tween 20). Tween 20) is preferably used in a concentration of at least 0.01 mg/ml. The non-ionic surfactant, if used, should preferably be present in an amount above the critical micelle concentration (CMC). See Wan and Lee, Journal of Pharm Sci, 63, p. 136, 1974.

Mono- or disaccharides (e.g. sucrose), polysaccharides such as low molecular weight dextrins, or sugar alcohols (e.g. sorbitol, glycerol or mannitol) may be added. The medicament may also comprise antioxidants such as bisulfite, ascorbate gluthathione, acetylcystein, tocopherol, methionin, EDTA, citric acid, butyl hydroxy toluene and /or butyl hydroxy anisole. Complexing agents, such as EDTA and citric acid can also be present in small concentrations for stabilising the FVIIa molecules, if they exhibit a stronger affinity for destabilising metal ions than for calcium or other divalent metal ions, e.g. zn2+. Furthermore, preservatives such as benzyl alcohol, phenol, sorbic acid, parabens, and chlorocresol may be added.

The adjuvants are generally present in a concentration of from 0.001 to 4% w/v. The pharmaceutical preparation may also contain protease inhibitors, e.g. aprotinin or tranexamic acid.

The pH of the preparation is preferably adjusted to a value in the interval of 2-9. Preparations having a pH from about 5.0 to about 7.5 are preferred, more preferred are preparations having a pH from about 5.0 to about 6.0, most preferred are preparations having a pH about 5.5.

Preferably, the used FVIIa is highly purified, i.e. has a specific activity of more than 40 IU/µg.

In one embodiment, the medicament consists of

| | |
|---|---|
| rFVIIa | 0.6 mg/ml (30,000 IU/ml) |
| Sodium chloride | 2.92 mg/ml |
| Glycylglycine | 1.32 mg/ml |
| Polysorbate 80 | 0.07 mg/ml |
| Calcium chloride, 2H2O | 1.47 mg/ml |
| Mannitol | 30.00 mg/ml |
| pH 5.5 | |
| (reconstituted with sterile water to 1 ml) | |

Conventional techniques for preparing pharmaceutical compositions, which can be used according to the present invention, are, for example, described in *Remington: The Science and Practice of Pharmacy*, 19$^{th}$ ed., 1995.

The medicaments may be sterilised by, for example, filtration through a bacteria-retaining filter, by incorporating sterilising agents into the medicaments, by irradiating the medicaments, or by heating the medicaments. They can also be manufactured in the form of sterile solid medicaments which can be dissolved in sterile water, or some other sterile injectable medium prior to or immediately before use.

The present invention is further illustrated by the following examples. The presented examples are meant as an illustration of the invention, not as a limitation.

EXAMPLES

Materials and Methods

The production of recombinant Factor VIIa (rFVIIa) was essentially performed as described in European Patent No. 200,421.

The FVIIa activity and the concentration were adjusted by dilution with water for injection and excipients were added in suitable amounts. The solution was then sterile filtered and freeze-dried.

Lyophilised powder of rFVIIa:

| | |
|---|---|
| rFVIIa | 0.6 mg/ml |
| Sodium chloride | 2.92 mg/ml |
| Glycylglycine | 1.32 mg/ml |
| Polysorbate 80 | 0.07 mg/ml |
| Calcium chloride, 2H2O | 1.47 mg/ml |
| Mannitol | 30.00 mg/ml |
| pH 5.5 | |

Prior to use, the lyophilised composition was reconstituted in water to a total volume of 1.0 ml.

Example 1

Animals

The study was performed in 4 female Göttingen minipigs from Ellegaard Göttingen Minipigs ApS, Sorø Landevej 302, DK-4261, Dalmose, Denmark. At start of the acclimatisation period the animals were 7 to 8 months old and the body weight was in the range 11.2 to 13 kg. A predosing period of one week (including an acclimatisation period of 5 days) was allowed before dosing.

Twice daily the animals were offered water and food (175 g Altromin 9023 for the first 2 days, thereafter 200 g).

The study was performed in a thermostated room at 21±3° C.

Drugs and Chemicals rFVIIa was used for dosing. The substance was dissolved in sterile H$_2$O to give 0.6 mg/ml. All other chemicals were obtained from commercial sources and were of analytical grade.

Experimental Design

The animals were dosed once intravenously (i.v.) and once subcutanously (s.c.) separated by a wash-out period of one week as follows:

| | Route of dosing | |
|---|---|---|
| Animal No. | First dosing | Second dosing |
| 1 | s.c. | i.v. |
| 2 | s.c. | i.v. |
| 3 | i.v. | s.c. |
| 4 | i.v. | s.c. |

The dose was 0.2 mg/kg body weight corresponding to 0.33 ml/kg body weight. The i.v. dose was given via a needle or a short catheter in an ear vein. Immediately after dosing the needle/catheter was flushed with 2-5 ml sterile, isotonic water.

The s.c. dose was given behind the pinna. The area of the dosing was marked with a colour marker.

Blood and Tissue Sampling

Blood samples were collected via needle puncture of the jugular vein/bijugular trunk. In connection with i.v. dosing the samples were collected before, and 6, 15, 30, 60 and 90 minutes and 2, 3, 4, 6 and 8 hours after dosing. Following s.c. dosing the samples were collected at 30, 60 minutes and 2, 3, 4, 5, 6, 8, 10, 12 14 and 24 hours as well as before dosing.

All blood samples were taken within 1 minute from stipulated time except for two samples (animal no. 4, 14 and 24 hours after s.c. dosing) that were taken 2 minutes after scheduled time.

The blood samples (3 ml) were collected in Vacutainers containing citrate for stabilisation and kept in ice-water until centrifugation (10 min, +4° C., about 1268×G). Two aliquots each of 150 TI were taken from each sample. To one of the aliquots 1350 TI of the buffer used for ELISA assay were added and the mixture devided between two Nunc Cryotubes labelled with "ELISA" appart from identification and stored at approximately −20° C. pending transfer to the Immunochemistry department for assay. To the other aliquot 1350 pl of the buffer used for Clot assay were added and the mixture devided between two Nunc Cryotubes. The tubes were labelled with "CLOT" apart from identification and stored at −80° C. pending transfer to the Immunochemistry department, Novo Nordisk, for assay. Buffer was added to the samples within 0.5 h after sampling and the samples were frozen within 1 h after sampling.

The day after the second dosing all animals were anaesthetized with an i.p. injection of mebumal and killed by exsanguination. The subcutaneous injection sites were located, examined macroscopically and representative samples were removed and fixed in phosphate buffered neutral 4% formaldehyde and transferred to the Pathology department, Novo Nordisk, for histopatological examination.

Analytical Methods

The concentration of rFVIIa was determined by an ELISA and the activity of rFVIIa by a Clot assay.

ELISA

The ELISA assay was FVII:Ag ELISA performed as described in Kit insert no. 1994.09/db version 1.0 (Danish version). The assay has previously been validated for human and rat plasma. A preliminary validation showed no indication of problems by using the assay for analysis in pig plasma. The assay is a two-site monoclonal immunoenzymatic assay using peroxidase as the marker enzyme. The microtiter wells are precoated with a specific anti-Factor VII monoclonal antibody. Thereafter both sample and enzyme-labelled antibody are added to the well. During the following step, a "sandwich" is formed between the solid-phase antibody, the Factor VII molecule and the enzyme-labelled specific Factor VII monoclonal antibody. Following a washing step, where unbound enzyme-labelled antibody is remove, the activity of the bound peroxidase is measured by enzyme's ability to transform a colourless substrate to a coloured product. The colour development is stopped by addition of sulphuric acid and is measured at 492 nm. As standard is used rFVIIa delivered with the assay. The calibration of the standard is based on absorbency measurement at 280 nm.

Clot-Assay

The Clot-assay was FVIIa:Clot (Stago) performed according to the kit insert. The assay has previously been validated for human and rat plasma. A preliminary validation showed no indication of problems by using the assay for analysis in pig plasma.

The recombinant soluble tissue Factor (rsTF) possesses a coFactor function specific for FVIIa. Consequently the FVII present in the test plasma does not interfere in the assay. The rsTF in the presence of FVIIa, phospholipids and $Ca^{++}$ produces coagulation of plasma. The observed clotting time bears an inverse relationship with the FVIIa level initially present in plasma. As standard is used rFVIIa delivered with the assay. The calibration of the standard is based on a comparison with the international FVIIa standard.

Analysis of Data

Results from ELISA as well as from Clot assay were subjected to non-compartmental pharmacokinetic analysis using the PC-based software WinNonlin (Scientific Consulting Inc.).

Results and Discussion

Results from the ELISA and Clot assays are given in Appendix A. Individual plasma concentration profiles are given in FIGS. 1 and 2. while individual pharmacokinetic parameters are given in Tables 1 and 2.

None of the predose samples had measurable concentrations or activities indicating sufficient wash-out between the two dosing periods.

The plasma concentration and activity profiles (FIG. 1-2) show an extended absorption phase following s.c. administration resulting in a $t_{max}$ mean of 6.5 (range 5-8 hours) and 4.0 (range 1.0-10.0) for concentration and activity, respectively.

TABLE 1

PK-Results from ELISA-Assay following Dosing 0.2 mg/kg (0.33 ml/kg) rFVII i.v. and s.c. to Minipigs Weighing 11.4-13.4 kg

| Animal | $C_{max}$ (ng/ml) | | $t_{max}$ (h) | $AUC_{0-\infty}$ (ng · h/ml) | | Extrapol. AUC (%) | | f (%) | Half-life (h) | |
|---|---|---|---|---|---|---|---|---|---|---|
| No. | i.v. | s.c. | s.c. | i.v. | s.c. | i.v. | s.c. | s.c. | i.v. | s.c. |
| 1 | 2130 | 86.3 | 8.0 | 4980 | 1711 | 11.2 | 14.7 | 34.4 | 2.7 | 7.7 |
| 2 | 2447 | 245.0 | 8.0 | 6960 | 4195 | 14.7 | 12.1 | 60.0 | 3.3 | 6.5 |
| 3 | 2134 | 142.6 | 5.0 | 6414 | 1849 | 13.0 | 12.7 | 28.8 | 2.9 | 7.2 |
| 4 | 2200 | 233.8 | 5.0 | 6659 | 2903 | 16.4 | 5.4 | 43.6 | 3.5 | 4.8 |
| Mean | 2228 | 176.9 | 6.5 | 6261 | 2665 | 13.8 | 11.2 | 41.7 | $3.5^a$ | $6.4^a$ |
| SD | 150 | 75.9 | 1.7 | 886 | 1151 | 2.3 | 4.0 | 13.6 | | |

[a] Harmonic mean

TABLE 2

PK-Results from Clot-Assay Following Dosing 0.2 mg/kg (0.33 ml/kg) rFVII i.v. and s.c. to Minipigs Weighing 11.4-13.4 kg

| Animal No. | $C_{max}$ (mIU/ml) i.v. | $C_{max}$ (mIU/ml) s.c. | $t_{max}$ (h) s.c. | $AUC_{0-\infty}$ (mIU·h/ml) i.v. | $AUC_{0-\infty}$ (mIU·h/ml) s.c. | Extrapol. AUC (%) i.v. | Extrapol. AUC (%) s.c. | f (%) s.c. | Half-life (h) i.v. | Half-life (h) s.c. |
|---|---|---|---|---|---|---|---|---|---|---|
| 1 | 161454 | 4609 | 2.0 | 201887 | 67038 | 7.0 | 11.4 | 33.2 | 2.6 | 6.9 |
| 2 | 183766 | 9155 | 10.0 | 274157 | 126227 | 4.9 | 5.0 | 46.0 | 2.3 | 4.7 |
| 3 | 156908 | 5415 | 3.0 | 240033 | 63730 | 6.7 | 12.0 | 26.6 | 2.6 | 7.0 |
| 4 | 149559 | 13355 | 1.0 | 249408 | 135294 | 12.4 | 8.1 | 54.2 | 3.6 | 6.4 |
| Mean | 162922 | 8134 | 4.0 | 241371 | 98073 | 7.8 | 9.1 | 40.0 | 2.7[a] | 6.1[a] |
| SD | 14735 | 4005 | 4.1 | 30001 | 37950 | 3.2 | 3.2 | 12.4 | | |

[a]Harmonic mean

Consequently, $C_{max}$ values were greatly reduced compared to those following i.v. administration (Tables 1 and 2). The AUCs following s.c. administration were reduced compared to those following i.v. administration (Tables 1 and 2). However, the extent of bioavailability was reasonably good as the mean f was 41.7% (range 28.8-60.0%) and 40.0% (range 26.6-54.2%) as estimated from ELISA and Clot assay results, respectively.

The half-life following s.c. administration was for all animals and for concentration as well as for activity results increased compared to that after i.v. administration (Tablea 1 and 2) The reason for that is most likely the so called "flip-flop" meaning that the rate of absorption is more slow than the rate of elimination. The half-life following s.c. administration is therefore a measure of the absorption rate rather than of the elimination rate.

Conclusion

The bioavailability of rFVIIa following subcutaneous administration to minipigs was sufficiently high to make this route of administration interesting in man. The absorption phase following s.c. administration was prolonged to an extent that might allow significantly increased dosing intervals in humans compared to those needed in connection with i.v. administration.

TABLE 3 rFVII Plasma Concentration and Activity Data

| | Results from ELISA (ng/ml) | | | | Resluts from Clot assay (mIU/ml) | | | |
|---|---|---|---|---|---|---|---|---|
| Time (h) | Pig 1 | Pig 2 | Pig 3 | Pig 4 | Pig 1 | Pig 2 | Pig 3 | Pig 4 |
| I.v. Adm. | | | | | | | | |
| 0 | <[a] | <[a] | <[a] | <[a] | <[b] | <[b] | <[b] | <[b] |
| 0.1 | 2129.9 | 2447.2 | 2134.1 | 2200 | 131950 | 169150 | 130260 | 125680 |
| 0.25 | 1713.9 | 2058.5 | 1921.7 | 1810.2 | 97488 | 149376 | 98528 | 96816 |
| 0.5 | 1389.5 | 1801.4 | 1699.7 | 1639.3 | 72332 | 106160 | 93384 | 81248 |
| 1 | 1151.5 | 1285.2 | 1336.5 | 1291.7 | 50155 | 67885 | 55860 | 50855 |
| 1.5 | 869.1 | 1157.9 | 1134.5 | 1167.8 | 36960 | 60625 | 59352 | 49193 |
| 2 | 669.4 | 1306.5 | 1023.2 | 1019.9 | 25011 | 36475 | 29230 | 33830 |
| 3 | 586.7 | 731.5 | 718.9 | 717.5 | 16349 | 29708 | 26200 | 26675 |
| 4 | 410.2 | 515.7 | 524.7 | 472.1 | 11149 | 13514 | 12923 | 12913 |
| 6 | 217.2 | 319.9 | 290.4 | 338.7 | 8641 | 7484 | 7812 | 9019 |
| 8 | 144.8 | 219.8 | 200.7 | 215.1 | 3813 | 4062 | 4364 | 5969 |
| s.c. Adm. | | | | | | | | |
| 0 | <[a] | <[a] | <[a] | <[a] | <[b] | <[b] | <[b] | <[b] |
| 0.5 | <[a] | 45.9 | <[a] | 68.6 | 3263 | 3889 | 1118 | 5904 |
| 1 | 53.5 | 84 | <[a] | 171.7 | 3907 | 6293 | 1990 | 13355 |
| 2 | 74.2 | 159.1 | 54.3 | 185.1 | 4609 | 8568 | 3509 | 11943 |
| 3 | 79.2 | 156.8 | 97.5 | 202.6 | 4315 | 6744 | 5415 | 12707 |
| 4 | 77.1 | 184.1 | 104.2 | 178.6 | 3889 | 7020 | 4510 | 10743 |
| 5 | 67.3 | 192.3 | 142.6 | 233.8 | 3108 | n.s. | 3589 | 7720 |
| 6 | 71.6 | 224 | <[a,c] | 178.6 | 2740 | 6663 | 1642 | 6591 |
| 8 | 86.3 | 245 | 109.8 | 122.7 | 2884 | 6927 | 3585 | 7000 |
| 10 | 79.8 | 225.8 | 91.9 | 140.4 | 3867 | 9155 | 3310 | 5630 |
| 12 | 58.4 | 193.3 | 69.9 | 118.6 | 2542 | 4983 | 2555 | 4700 |
| 14 | 75.6 | 161.9 | 60.5 | 106.6 | 2066 | 4543 | 1977 | 2970 |
| 24 | 22.5 | 54.4 | 22.5 | 22.5 | 764 | 929 | 759 | 1180 |

[a]Below limit of quantitation (45 ng/ml)
[b]Below limit of quantitation (117.6 mIU/ml)
[c]Excluded as outliner
n.s.: No sample

The invention claimed is:

1. A method for treatment of a condition affectable by Factor VIIa (FVIIa), said method comprising administering subcutaneously to a mammal in need of such treatment an effective amount for treating said condition of a composition comprising modified FVIIa, wherein said modified FVIIa has substantially the same or better biological activity for blood coagulation as authentic FVIIa.

2. The method of claim 1, wherein the condition is bleeding caused by a lack of, or defect in, coagulation factors VIII, IX, or VII, or by the presence of inhibitors against coagulation factors VIII, IX, or VII.

3. The method of claim 1, wherein the condition is haemophilia A or B.

4. The method of claim 1, wherein the modified FVIIa is modified recombinant human FVIIa.

5. The method of claim 1, wherein the composition is a stable aqueous solution ready for administration.

6. The method of claim 1, wherein the composition is lyophilized and reconstituted with a pharmaceutically acceptable vehicle suitable for injection prior to administration.

7. The method of claim 1, wherein the composition is a stable aqueous solution ready for administration.

8. The method of claim 1, wherein the modified FVII is selected from the group consisting of: [S52A]-FVIIa, [S60A]-FVIIa; Factor VIIa that has been proteolytically cleaved between residues 290 and 291; Factor VIIa that has been proteolytically cleaved between residues 315 and 316; [L305V]-FVIIa; [L305V/M306D/D309S]-FVIIa; [L305I]-FVIIa,[L305T]-FVIIa; [F374P]-FVIIa; [V158T/M298Q]-FVIIaI; [V158D/E296V/M298Q]-FVIIa and [K337A]-FVIIa.

* * * * *

SEQUENCE LISTING

<160> NUMBER OF SEQ ID NOS: 1

<210> SEQ ID NO 1
<211> LENGTH: 406
<212> TYPE: PRT
<213> ORGANISM: Homo sapiens
<220> FEATURE:
<221> NAME/KEY: MISC_FEATURE
<222> LOCATION: (1)..(406)
<223> OTHER INFORMATION: Xaa= 4 - carboxyglutamic acid (gamma - carboxyglutamate)

<400> SEQUENCE: 1

```
Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335
```

```
Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405
```